United States Patent
Elhasid (10) Patent No.: US 12,257,100 B2
(45) Date of Patent: Mar. 25, 2025

(54) ORAL DEVICE FOR MEASURING RESPIRATORY SOUNDS

(71) Applicant: OmnySense Ltd., Tel-Aviv (IL)

(72) Inventor: Amir Elhasid, Hod HaSharon (IL)

(73) Assignee: OmnySense Ltd., Tel-Aviv (IL)

( * ) Notice: Subject to any disclaimer, the term of this patent is extended or adjusted under 35 U.S.C. 154(b) by 467 days.

(21) Appl. No.: 17/763,545

(22) PCT Filed: Sep. 24, 2020

(86) PCT No.: PCT/IL2020/051054
§ 371 (c)(1),
(2) Date: Mar. 24, 2022

(87) PCT Pub. No.: WO2021/059284
PCT Pub. Date: Apr. 1, 2021

(65) Prior Publication Data
US 2022/0401059 A1 Dec. 22, 2022

Related U.S. Application Data

(60) Provisional application No. 62/905,516, filed on Sep. 25, 2019.

(51) Int. Cl.
*A61B 7/00* (2006.01)
*A61B 5/00* (2006.01)
(Continued)

(52) U.S. Cl.
CPC ............ *A61B 7/003* (2013.01); *A61B 5/0022* (2013.01); *A61B 5/01* (2013.01); *A61B 5/4842* (2013.01);
(Continued)

(58) Field of Classification Search
None
See application file for complete search history.

(56) References Cited

U.S. PATENT DOCUMENTS 3,884,219 A * 5/1975 Richardson ........ A61B 5/02055
600/537
3,999,537 A * 12/1976 Noiles .................... A61B 5/274
374/E13.002

(Continued)

FOREIGN PATENT DOCUMENTS

CN 105534544 A 5/2016
CN 107635459 A 1/2018
(Continued)

OTHER PUBLICATIONS

Search strategy for PCT/IL2020/051054 dated Jan. 12, 2021.
(Continued)

*Primary Examiner* — Michael R Bloch
(74) *Attorney, Agent, or Firm* — The Roy Gross Law Firm, LLC; Roy Gross (57) ABSTRACT

The invention relates to a thermometer-shaped oral device for measuring respiratory sounds. The oral device comprises a mouthpiece with a metallic tip for placement under the tongue and a neck around which the lips seal the mouth closed, preventing outside noises from interfering with the measurement of the respiratory sounds. The oral device performs the auscultatory function traditionally performed by a stethoscope. The metallic tip may contain a thermistor for oral temperature measurement, and in various embodiments the oral device may further comprise other vital signs sensors. The oral device may be in communication with a cloud server, as part of a system for remote auscultation by a physician and/or analysis of auscultation and/or other vital signs by a healthcare bot for detecting progression of respiratory or other diseases.

21 Claims, 9 Drawing Sheets

(51) Int. Cl.
  *A61B 5/01*    (2006.01)
  *A61B 7/04*    (2006.01)
  *G16H 10/60*   (2018.01)
  *G16H 40/67*   (2018.01)
  *G16H 50/20*   (2018.01)
  *G16H 50/30*   (2018.01)
  *G16Y 10/60*   (2020.01)
  *G16Y 20/40*   (2020.01)
  *G16Y 40/10*   (2020.01)
  *G16Y 40/20*   (2020.01)
  *H04L 67/12*   (2022.01)
  *A61B 5/08*    (2006.01)

(52) U.S. Cl.
  CPC .............. *A61B 5/682* (2013.01); *A61B 7/04* (2013.01); *G16H 10/60* (2018.01); *G16H 40/67* (2018.01); *G16H 50/20* (2018.01); *G16H 50/30* (2018.01); *G16Y 10/60* (2020.01); *G16Y 20/40* (2020.01); *G16Y 40/10* (2020.01); *G16Y 40/20* (2020.01); *H04L 67/12* (2013.01); *A61B 5/0816* (2013.01); *A61B 5/742* (2013.01)

(56) References Cited

U.S. PATENT DOCUMENTS

| | | | | |
|---|---|---|---|---|
| 4,036,211 | A * | 7/1977 | Veth | A61B 5/0816 600/479 |
| 4,202,353 | A * | 5/1980 | Hirsch | G01F 1/6842 374/E13.002 |
| 4,715,367 | A | 12/1987 | Crossley | |
| 5,056,514 | A | 10/1991 | DuPont | |
| 5,642,735 | A * | 7/1997 | Kolbly | A61B 5/0878 600/549 |
| 7,912,536 | B2 * | 3/2011 | Fendrock | A61B 5/25 600/513 |
| 2004/0019293 | A1 * | 1/2004 | Schweitzer, Jr. | A61B 5/14552 600/549 |
| 2004/0039295 | A1 | 2/2004 | Olbrich et al. | |
| 2004/0163648 | A1 | 8/2004 | Burton | |
| 2005/0096558 | A1 * | 5/2005 | Friedman | A61B 5/0816 374/E13.002 |
| 2008/0281220 | A1 * | 11/2008 | Sharifpour | G16H 50/20 600/538 |
| 2011/0092839 | A1 | 4/2011 | Alshaer et al. | |
| 2013/0253286 | A1 * | 9/2013 | Fridman | A61B 5/02055 600/301 |
| 2013/0253357 | A1 | 9/2013 | Moussavi et al. | |
| 2015/0045629 | A1 * | 2/2015 | Azimi | A61B 5/02055 600/301 |
| 2016/0242701 | A1 * | 8/2016 | Gonnen | A61B 5/7257 |
| 2017/0238815 | A1 * | 8/2017 | Luxon | A61B 5/02055 |
| 2018/0020976 | A1 * | 1/2018 | Yossi | A61B 5/01 600/301 |
| 2018/0110418 | A1 * | 4/2018 | Fridman | G16H 10/40 |
| 2018/0140252 | A1 * | 5/2018 | Luxon | A61B 5/02416 |
| 2019/0261889 | A1 | 8/2019 | White | |

FOREIGN PATENT DOCUMENTS

| | | |
|---|---|---|
| DE | 2948863 A1 | 6/1981 |
| EP | 2835100 A1 | 2/2015 |
| GB | 1313486 A | 4/1973 |
| JP | 2018503493 A | 2/2018 |
| JP | 2019500084 A | 1/2019 |
| WO | 2016120875 A1 | 8/2016 |
| WO | 2017087366 A1 | 5/2017 |
| WO | 2017112960 A1 | 6/2017 |

OTHER PUBLICATIONS

International search report for PCT/IL2020/051054 dated Jan. 14, 2021.
Written opinion for PCT/IL2020/051054 dated Jan. 14, 2021.
International preliminary report for PCT/IL2020/051054 dated Feb. 21, 2022.
European Patent Office, Supplementary European Search Report for European Patent Application No. EP 20870287.8, dated Mar. 21, 2024, 8pp.
Japanese Patent Office, Office Action for Japanese Patent Application No. 2022-529724, dated Jun. 18, 2024, 11pp.
The State Intellectual Property Office of the People's Republic of China, The First Office Action for Chinese Patent Application No. 202080082016.5, dated Nov. 28, 2024, 21pp.

* cited by examiner

ORAL DEVICE FOR MEASURING RESPIRATORY SOUNDS

CROSS REFERENCE TO RELATED APPLICATIONS

This application is a National Phase of PCT Patent Application No. PCT/IL2020/051054 having International filing date of Sep. 24, 2020, which claims the benefit of priority of U.S. Provisional Patent Application No. 62/905,516, filed Sep. 25, 2019, the contents of which are all incorporated herein by reference in their entirety.

FIELD OF THE INVENTION

The present invention is in the field of medical devices for detecting respiratory sounds. Specifically, it describes an enhanced thermometer-like device which detects respiratory sounds in the oral cavity, in order to collect these sounds during a thermometer reading, for subsequent analysis.

BACKGROUND TO THE INVENTION

Respiratory sounds, including lung and airways sounds, can serve to diagnose respiratory conditions and enable the progression of respiratory disease to be monitored. Typical lung sounds associated with specific respiratory conditions include different types of wheezes, or crackles or combinations thereof that characterize asthma, chronic obstructive pulmonary disease (COPD), bronchiolitis, cystic fibrosis and Pulmonary arterial hypertension (PAH). For example, wheezing is one of the most common symptoms in asthma. In its mildest form, the wheezing is only present during the late-expiratory phase. As the severity increases, the wheeze lasts throughout expiration. During a more severe asthmatic episode, wheezing is also present during inspiration. Coarse crackles at the early-inspiratory phase are commonly heard in patients with COPD and in patients with chronic bronchitis. Fine crackles are detected in the majority of patients with IPF.

These lung sounds are traditionally monitored via auscultation; i.e. by using a stethoscope held against the chest and/or back, by a qualified physician. More recently, electronic stethoscopes for auscultation have started to be used, with electronic processing of the results in order to better identify features, and potentially to store the history. Electronic stethoscopes comprise a membrane held against the skin where this membrane is coupled with a sensitive microphone such as an electret microphone, where this microphone is connected to an amplifier.

SUMMARY OF THE INVENTION

While suitable for physicians, electronic stethoscopes are unfamiliar to untrained patients and caretakers, and difficult for them to use. Accordingly, when considering home use and connection to telemedicine systems, there is a need for a simpler and more familiar method to detect and record sounds from the respiratory system and enable their transmission to remote health systems and physicians. Furthermore, there is a need for a system enabling auscultation for this purpose, that would be usable by an untrained patient with minimal effort.

A device of the present invention is a thermometer-shaped device whose structure is such that it is capable of recording respiratory sounds detected within the oronasal cavity. The oronasal cavity is the structure comprising the oral and nasal structures within the head, and it constitutes the upper end of the respiratory system. As opposed to detecting the sounds within the respiratory system externally across the skin to a microphone (i.e. via conventional auscultation), the device of the present invention records these sounds from within the respiratory system. Advantageously, as the device is thermometer-shaped, it is known and acceptable to patients and its use is familiar. Furthermore, the fact that a thermometer is used with the mouth closed, ensures that the sound conveyed from the lungs (via the trachea) is undisturbed by external sounds; enabling the functional-equivalent of lung auscultation to be performed.

Note also that auscultation is also used for listening to heart sounds. Heart sounds are created due to opening and closure of the valves, blood flow through orifices, flow of blood into the ventricular chambers, and rubbing of the cardiac surfaces. Heart sound frequencies can be impacted by valve apparatus; however, they normally range from 10 to 200 Hz. By appropriate signal differentiation, the heart sounds detected by the present invention can also be recorded and processed.

An additional advantage that results from the approach of using a thermometer-shaped device is that such a device is also a good platform for measuring additional medical parameters. In some embodiments, the device contains an oral temperature sensor in its tip—as does a standard thermometer. In a further preferred embodiment, the device will also incorporate a reflective pulse oximetry sensor. In a further preferred embodiment, the device will also incorporate electrocardiogram (ECG) electrodes as per PCT/IL2020/050874, hereby incorporated by reference.

Respiratory sounds collected can be analyzed to yield the respiratory rate. In a further preferred embodiment these sounds can serve to extract lung sounds. This analysis can take place within the device, and/or the signals can be transmitted to a smartphone for analysis and/or transmitted onwards to a remote location for storage and/or analysis.

The object of the invention is to provide a simple and easy-to-use method of detecting and recording sounds from the respiratory system, suitable for use by untrained patients in their home environment.

It is a further object of the invention to calculate the respiratory rate and I:E ratio from the recorded sounds.

It is a still further object of the invention to extract respiratory and/or lung sounds and transmit them to a remote server or physician.

It is a still further object of the invention to analyze the changes in the respiratory and/or lung sounds over time, as a way of monitoring disease progression.

It is a still further object of the invention to measure additional physiological parameters at the time that the respiratory and/or lung sounds are collected, so as to provide a broad set of physiological data for analysis.

It is a still further object of the invention to provide a thermometer-shaped oral device for recording respiratory sounds, comprising a mouthpiece containing one or more microphones, the mouthpiece configured for insertion into a patient's mouth, whereby the microphones detect the respiratory sounds from the patient's oronasal cavity.

It is a still further object of the invention to provide the abovementioned oral device, wherein the mouthpiece comprises a metallic tip for sensing oral temperature.

It is a still further object of the invention to provide the abovementioned oral device, further comprising a display.

It is a still further object of the invention to provide the abovementioned oral device, wherein the display displays respiratory rate and oral temperature of the patient.

It is a still further object of the invention to provide the abovementioned oral device, further comprising an ECG, a pulse oximetry sensor, or any combination thereof.

It is a still further object of the invention to provide the abovementioned oral device, wherein the device enables the functional-equivalent of lung auscultation.

It is a still further object of the invention to provide the abovementioned oral device, further comprising other components of a system for remote measurement of lung auscultation and/or other vital signs, the system further comprising a cloud server in wireless communicative connection with the oral device; the cloud server is configured to upload and store the lung auscultation and/or vital signs data; the cloud server is communicative connection with a display device of medical personnel.

It is a still further object of the invention to provide the abovementioned oral device, wherein the wireless connection comprises a 5G modem, a SIM module, BLUETOOTH®/BLUETOOTH® Low Energy, Wi-Fi®, cellular, or any combination thereof.

It is a still further object of the invention to provide the abovementioned oral device, wherein the cloud server comprises one or more healthcare bots for analysis of the lung auscultation for evidence of progression of a disease.

It is a still further object of the invention to provide the abovementioned oral device, further configured to display the auscultation, its analysis, or any combination thereof on the display device.

It is a still further object of the invention to provide a method of remotely analyzing disease progression with the abovementioned system.

It is a still further object of the invention to provide the abovementioned method, wherein the analyzing of disease progression is further a function of other vital signs data recorded by the oral device.

It is a still further object of the invention to provide the abovementioned method, wherein the other vital signs comprise temperature, ECG data, pulse oximetry data, or any combination thereof.

It is a still further object of the invention to provide a method of performing remote auscultation based on the abovementioned system.

DETAILED DESCRIPTION OF EMBODIMENTS

Definition: As exemplified in FIG. 1, a "thermometer-shaped device" 1 comprises a handle section 2 and a mouthpiece comprising a neck 3 and a tip 4. The tip 4 is configured for placement under the tongue and the neck 3 is configured for being wrapped around and sealed by the lips.

Figure 2:
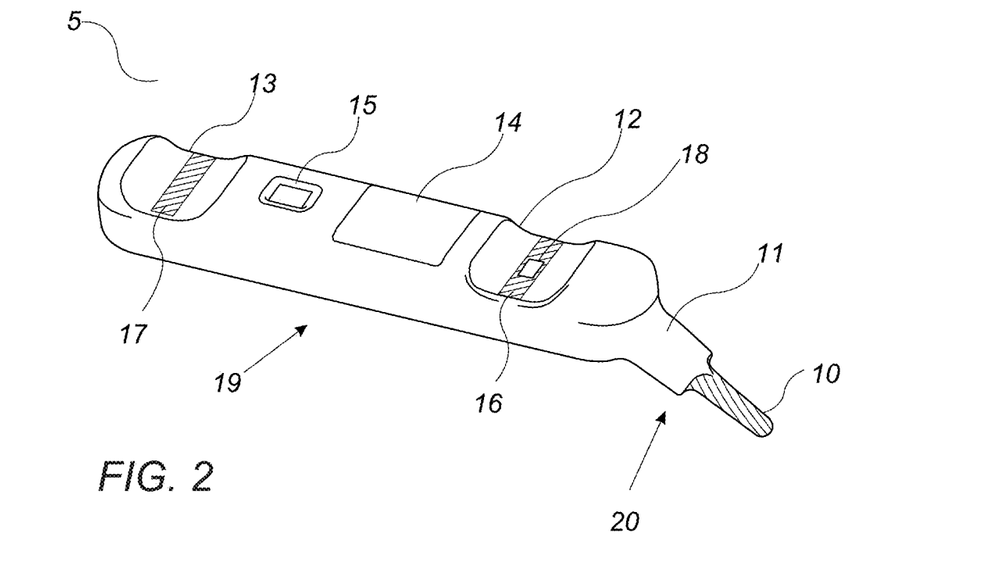
FIG. 2 provides a view of an oral device for detecting respiratory and/or lung sounds, according to some embodiments of the invention.

Reference is now made to FIG. 2, showing a preferred embodiment of the device 5 of the present invention. The device 5 comprises a handle section 19 and a mouthpiece 20. The mouthpiece 20 contains an assembly for the detection and recording of respiratory and lung sounds when it is placed in the patient's mouth. When the tip 10 of the mouthpiece 20 is placed under the patient's tongue, the patient's lips close around a neck 11 of the mouthpiece 20, creating a sound box reaching from the lungs to the oronasal cavity, via the trachea. Thus, the action of placing the device in the mouth enables the detection of respiratory and lung sounds to take place. In some embodiments, the tip 10 contains a thermistor for taking of the patient's temperature. Suitable thermistors for the oral temperature-sensing include the MF51E2252F3950C bead type thermistor from Cantherm (Montreal, Canada).

Figure 5:
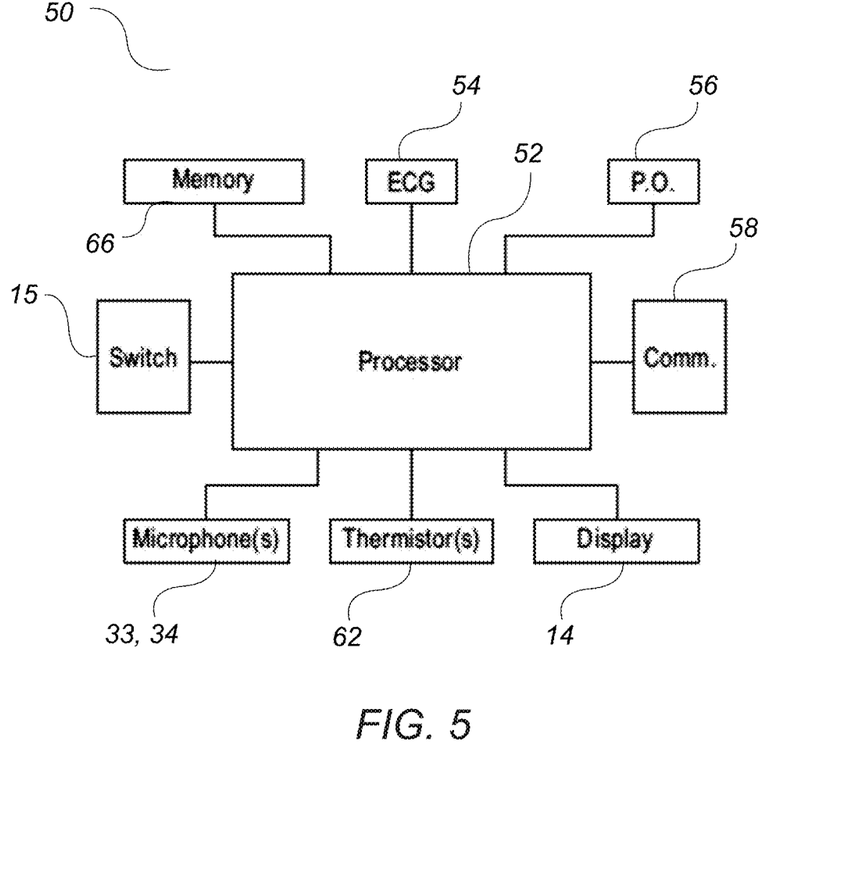
FIG. 5 shows a functional block diagram a control circuit of the oral device, according to some embodiments of the invention.

In some embodiments, the oral device 5 further comprises an ECG circuit and/or pulse oximetry sensor, wherein the handle section 19 comprises two grasping points 12, 13 for holding the device, a display 14, an activation button 15, two electrode contacts 16, 17 and a pulse oximetry sensor 18. Located within the device is an internal electronics board (PCB) containing a control circuit 50 whose block diagram is shown in FIG. 5. The control circuit 50 processes the signals measured from the various sensors and optionally transmits all or part of the signals data to an external device such as a smartphone (not shown).

Figure 3A:
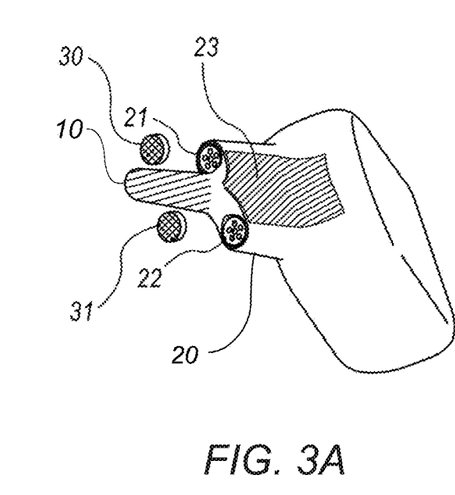
FIGS. 3A and 3B show external exploded and assembled views, respectively, of the mouthpiece of the oral device, according to some embodiments of the invention.
Figure 3B:
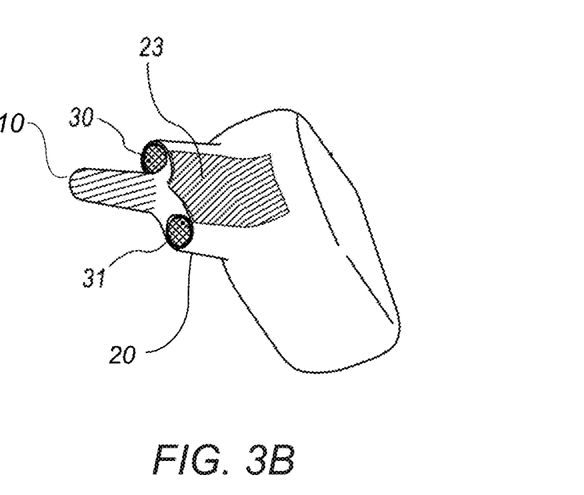
Figure 4A:
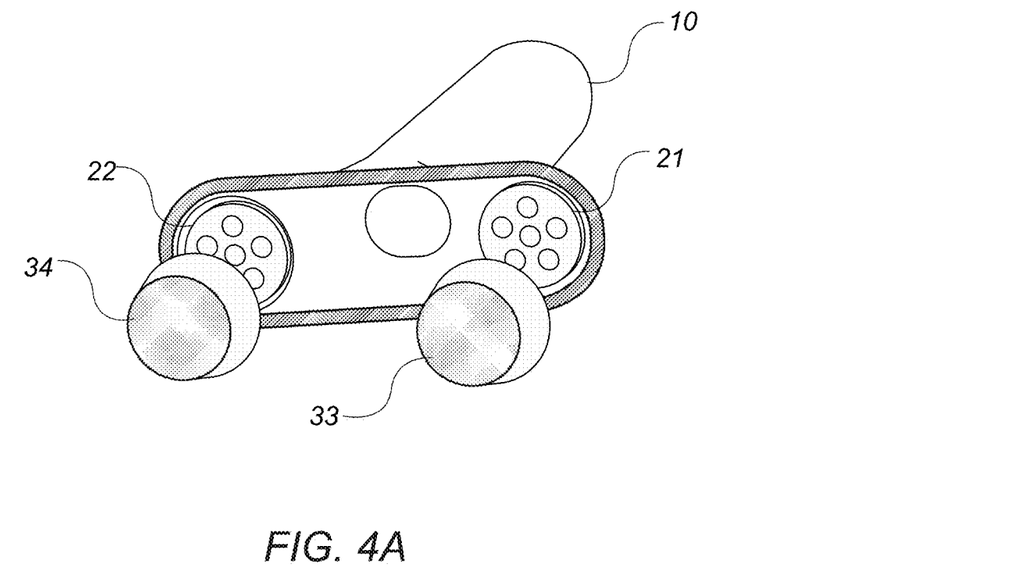
FIGS. 4A and 4B show internal exploded and assembled views, respectively, of the mouthpiece, according to some embodiments of the invention.
Figure 4B:
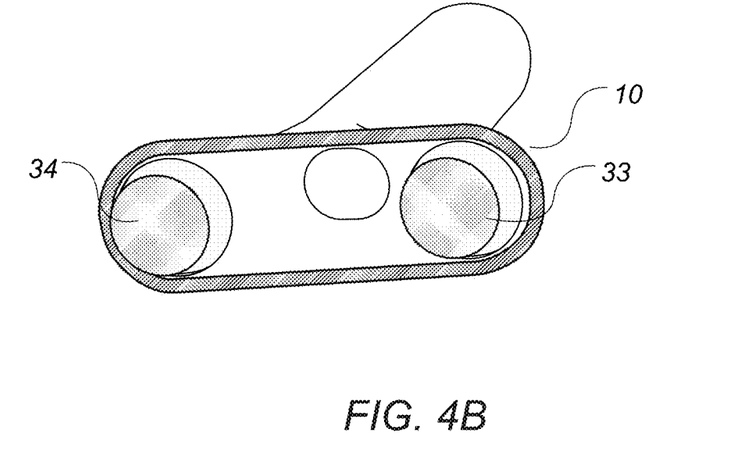

Reference is now made to FIGS. 3A and 3B, showing external exploded and assembled views, respectively, of the mouthpiece 20, according to some embodiments of the invention; as well as FIGS. 4A and 4B, showing internal exploded and assembled views, respectively, of the mouthpiece 20, according to some embodiments of the invention. The mouthpiece 10 contains one or more in-mouth microphones 33 and 34, for listening to respiratory sounds. When the mouthpiece 20 is inserted into the mouth, the tip 10 is placed under the tongue and the lips rest against the neck 11. When the lips are thus sealed around the mouthpiece 20 of the oral device 5, acoustic access holes 21 and 22 are located within the mouth and thus exposed to the sounds detectable therein.

Acoustic access holes 21, 22 can be slightly recessed, such that there is a place to insert a disc of an air/liquid filter material 30 and 31, where the microphones 33, 34 are mounted inside the mouthpiece on the other side of the holes 21, 22. This arrangement prevents the entry of liquid into the microphones, while ensuring that the microphones are able to pick up the sounds detectable within the oral cavity. It is possible to use a plurality of microphones for this purpose, with the sounds analyzed potentially representing the sum (or some other function) of the sounds detected by the microphones. One advantage of using two microphones is that, in the event that one gives a clear signal and the other seems blocked—for example by the tongue—then the stronger signal can be used. Suitable potential microphones for this purpose include digital microphones like the MP34DT06J PDM-type microphone from STMicroelectronics NV (Eindhoven, Holland); and sensitive analog microphones such as the CMC-4015-25L 100 electret condenser microphone from CUI Devices (Lake Oswego, OR, USA). An example of a suitable material for the air/liquid filters 30, 31 are hydrophobic membranes from W. L. Gore & Associates, Inc. (Newark, DE, USA).

Reference is now made to FIG. 5, showing a functional block diagram of the control circuit 50 of the oral device 5, according to some embodiments of the invention. In preferred embodiments, the microphones 33, 34 are digital, such that they can be interfaced directly into the bus of the processor 52. For this preferred embodiment, an example processor 52 is the Cypress BLUETOOTH® Low Energy microprocessor module CYBLE-416045-02 from Cypress Semiconductor Corp. (San Jose, CA, USA) may be used. Advantageously, the Cypress processor contains an integrated BLUETOOTH® Low-Energy (BLE) module, thereby obviating the need to incorporate a separate communications chip 58 in the control circuit 50. Advantageously, the thermistor(s) 62 described above can also be connected directly to the Cypress processor, using its internal A/D conversion channels.

The ECG electrodes 16, 17 on the body 19 of the device are interfaced to an ECG chip 54, which is interfaced digitally into the microprocessor 52. In a preferred embodiment of the circuit, a single chip contains both the ECG module 54 and the pulse oximetry module 56, of which the sensor 18 is a part. An example integrated sensor chip of this type is the MAX86150 chip from Maxim Integrated (San Jose, CA, USA). Advantageously, by building the circuit around just two main chips—an integrated microprocessor plus BLUETOOTH® Low Energy module and an integrated sensor chip—the complexity is reduced while the costs are minimized. Suitable displays for the device of the present invention include liquid crystal displays (LCDs) and light emitting diodes (LEDs), for example the 1.44" graphical TFT-type LCD display model KSF128128A0-1.44, from KSF Ltd. (Hong Kong).

Operation of the device of the present invention to detect and record respiratory and lung sounds, in preferred embodiments, proceeds as follows. After activating the device using its switch, the patient grasps the device, preferably using the grasping positions 12 and 13, and places the mouthpiece in his mouth such that the oral-temperature tip is under his/her tongue and his/her lips are closed around the neck 11. It is recommended to use the grasping positions such that a finger rests in the recess while the opposable thumb presses against the underside of the device at that place. After approximately 20-30 seconds, the device issues a beep and/or an indication on the display 14, to signal that the "temperature reading" is complete. Note that, due to the thermometer-type design of the device, the measurements taken during this time include (as a minimum) both oral temperature and a recording of the sounds detected within the mouth by the microphone during this period. A digital recording of these sounds, at the resolution and sampling rate chosen (for example 12 bits at 4 kHz), is stored in the memory 66 of the control circuit 50 and/or transmitted via the communications module to a computer or smartphone (not shown), or uploaded to the internet (for example over the personal area network protocol Wi-Fix (IEEE 802.11x standards)). In preferred embodiments, the data is transmitted over the wireless network protocol BLUETOOTH® Low Energy to a smartphone for recording and uploading to a remote computer system. This configuration enables a remote physician to listen to the sounds recorded and analyze them. As physicians typically perform auscultation for only a few seconds at any given body location, it will typically be sufficient to record and forward between 5 and 10 seconds of the sound recording taken by the device of the present invention.

Figure 6:
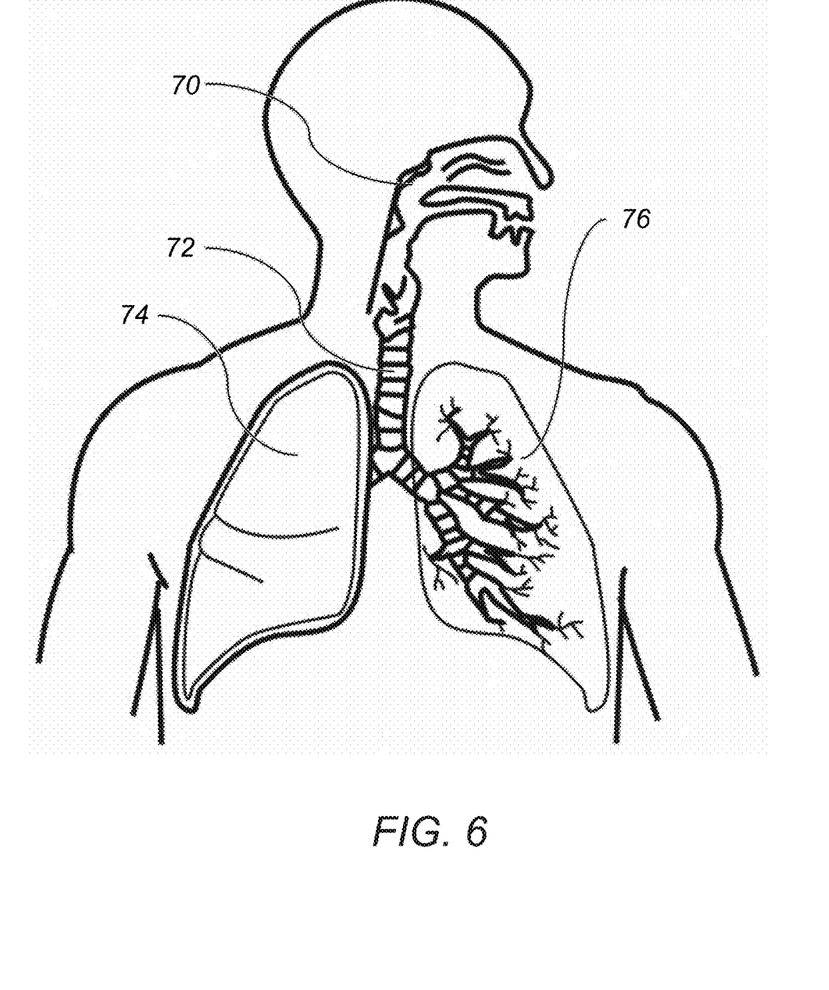
FIG. 6 shows a schematic view of the entire respiratory system, from the oronasal cavity, through the trachea, and to the lungs.

Reference is now made to FIG. 6. The respiratory system extends from the oronasal cavity 70, down through the trachea 72 to the lungs 74. Also shown is the internal structure 76 of the lungs. Advantageously, as the microphones 33, 34 are located within the respiratory system, it is possible to detect the respiratory sounds within the entire respiratory system. Additionally, and synergistically with the standard use of a thermometer, the mouth is kept closed by the patient for the duration of the temperature reading, thereby increasing the degree to which the respiratory and lung sounds are trapped within a mostly closed space and external interference is reduced. A key advantage of the present invention is that this sound detection is performed internally within the body, as opposed to requiring an external membrane interface external to the body (as is the case when a stethoscope is used). In this manner, the present invention serves to enable the functional equivalent of lung auscultation to be performed, but without the use of a stethoscope.

Figure 7:
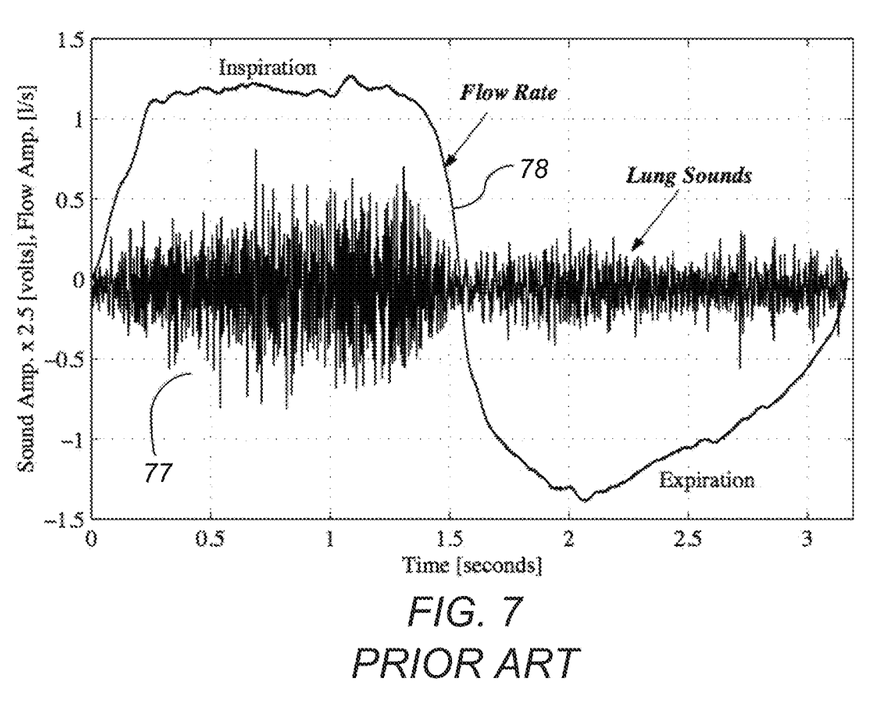
FIG. 7 shows an example of a waveform of the sounds generated by the respiratory system.

Reference is now made to FIG. 7, showing a typical waveform 77 of lung sounds detected by chest auscultation of a single respiratory cycle, taken by a conventional digital stethoscope. (In the Experimental section below, the digital stethoscope waveform 77 shall be compared with waveforms from the oral device 5.) The waveform is overlaid by an air flow plot 78 (inspirium/experium) detected at the mouth. It is noted that there is a low-frequency periodicity associated with the breathing action (typically 10-15 breaths/min in an adult), and higher-frequency lung sounds are detectable during both the inhalation and expiration phases of each breath.

The low-frequency wave shown is isolated in order to calculate the patient's respiratory rate and I:E ratio. Respiratory rate is an important vital sign, and so, in a preferred embodiment, this rate is calculated within the control circuit 50 of the device and displayed on its internal display 14.

Figure 1:
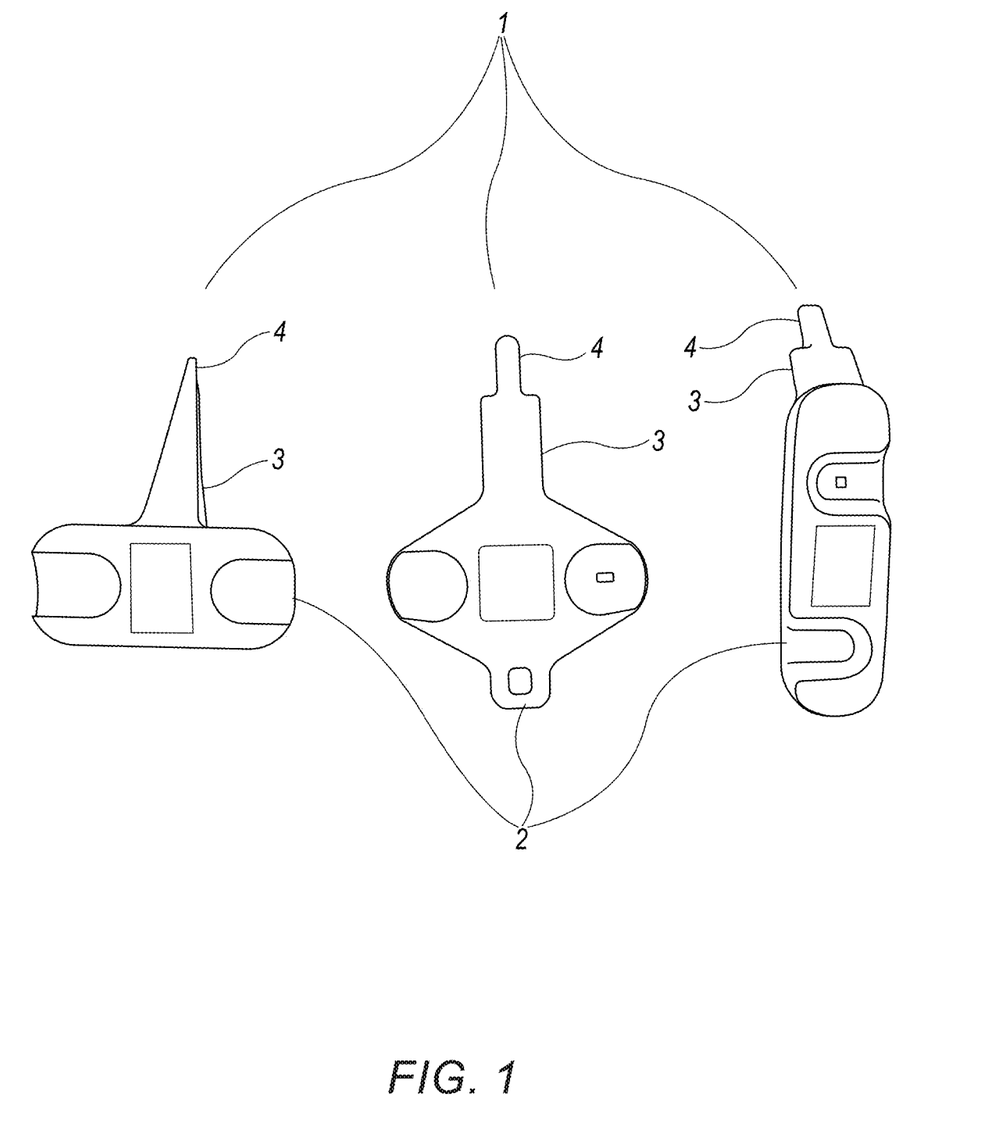
FIG. 1 provides a view of exemplary embodiments of a thermometer-shaped device, as defined in the present disclosure.

The oral device 5 shown in FIG. 1, measures and displays the respiratory rate and the oral-temperature. In some embodiments, additional sensors detect and enable display of further medical parameters. A pulse oximetry sensor 18 can be located along a finger grasping location (either 12 or 13). In this configuration, when the patient grasps the oral device 5 as instructed, his/her pulse rate and peripheral oxygen saturation ($SpO_2$) parameters will be measured by the pulse oximeter while the temperature reading is underway. In a preferred embodiment, these data are also be shown on the display 14 of the device; such that it is possible to display the four vital signs: temperature, respiratory rate, pulse rate and $SpO_2$ on the display. The vital signs may either be displayed simultaneously or, for example, by using a switch 15 to toggle between showing the different parameters.

Similarly, during the time that the patient is holding the device in his/her mouth to perform the temperature measurement, if the patient is holding the device as instructed, with a finger of each hand in the grasping places 12, 13, then the electrodes 16, 17, located in the grasping areas 12, 13 enable an ECG reading to be taken at the same time. The electrodes 16, 17 are connected to the ECG chip 54 described in conjunction with the block diagram shown in FIG. 4. In some embodiments, an additional third electrode is applied at the mouth, either via a metallic section 23 on the mouthpiece 20, or by using the metallic tip 10 which houses the temperature sensor. Where a three-electrode configuration is used—one on each finger and one in the mouth—the ECG trace generated may be calculated according to the description given in co-pending patent PCT/IL2020/050874.

Thus, by proper use of an oral device 5 of the present invention, a large number of medical parameters may be measured simultaneously. Any or all of this information may be transmitted via the communications module to a remote computer, via a smartphone or any other suitable means.

The lung sounds detected by an oral device 5 of the present invention can serve to diagnose respiratory conditions and enable the progression of respiratory disease to be monitored. As described above, typical lung sounds associated with specific respiratory conditions include different types of wheezes, crackles, or combinations thereof which can serve to characterize asthma, COPD, bronchiolitis, cystic fibrosis and PAH. For example, asthma is typically identified by the combination of early inspiratory crackles and late inspiratory fine crackles, whereas bronchiectasis can be identified by wet crackles. Similarly, the combination of a mid-inspiratory wheeze and a mid-expiratory wheeze suggests bronchiolar disease.

In a similar manner, specific heart sounds detected via the device can also be indicative of cardiac conditions, and their worsening can indicate deterioration.

Figure 8:
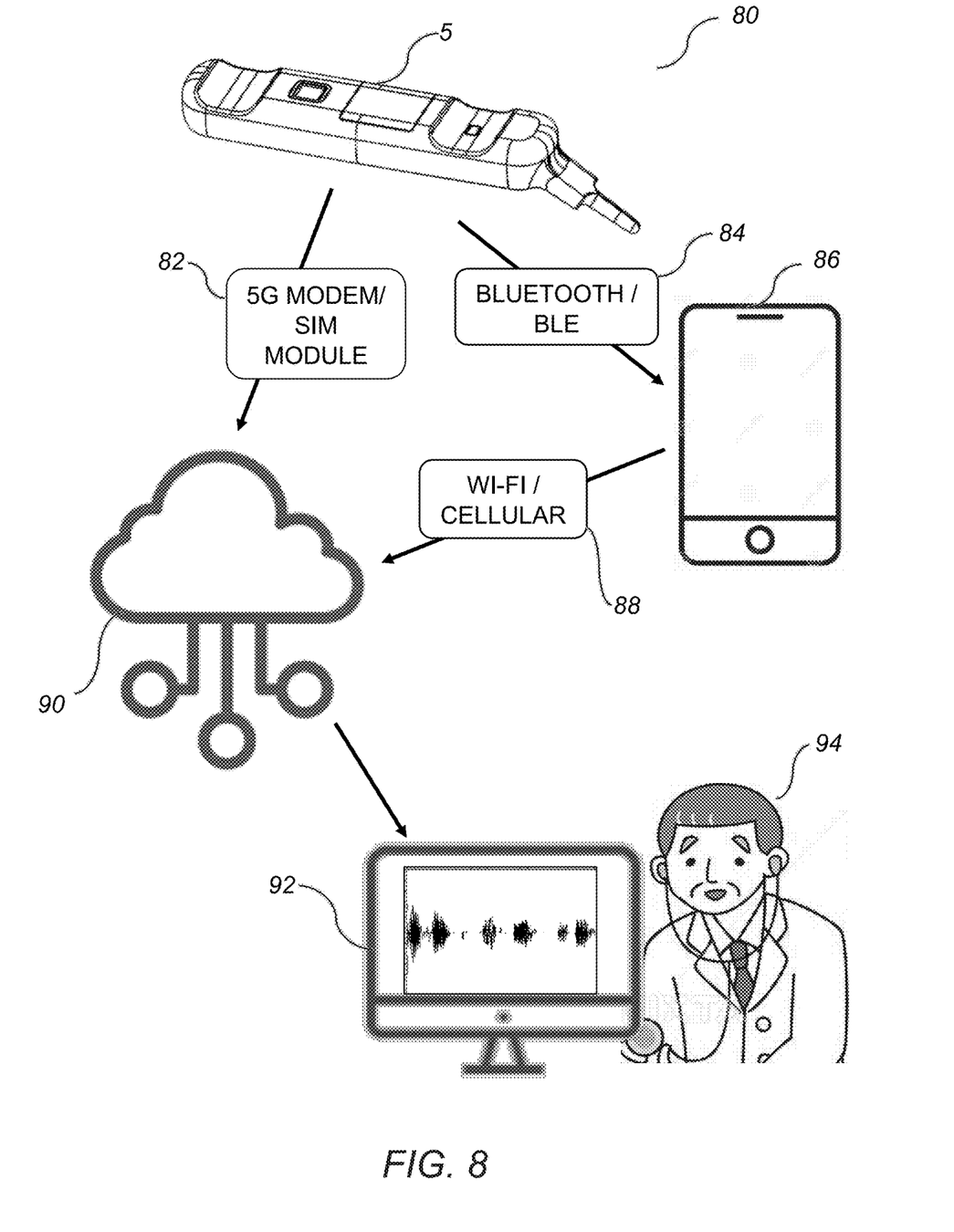
FIG. 8 shows a functional block diagram of a system for remote measurement of lung auscultation and/or other vital signs.

Reference is now made to FIG. 8, showing a functional block diagram of a system 80 for remote measurement of lung auscultation and/or other vital signs. The oral device 5 digitally samples the lung sounds and transmits the sampled data wirelessly to a cloud server 90. For example, the data may be transmitted from the oral device 5 by a SIM module or 5G modem 82; or, for example, by BLUETOOTH®/BLUETOOTH® Low Energy 84 to a smartphone 86 and then via Wi-Fix or cellular 88 from the smartphone 86 to the cloud server 90. The cloud server 90 uploads and stores the sampled data, for transmission to a physician or computer analysis, as further described herein. Alternatively, some or all analysis may be performed within the control circuit 50 and/or the smartphone 86. The control circuit 50, smartphone 86, or cloud server 90 may timestamp the sampled data.

A display device 92, connected to the cloud server 90, of medical personnel 94 can display the auscultation waveform to the medical personnel 94 for remotely monitoring a patient. Alternatively, or in addition, a healthcare bot can monitor and analyze changes in the sounds over time. For example, a healthcare bot within or accessible to the cloud server 90 may analyze an auscultation waveform of a patient over time for indications of disease progression. In particular, numerical indices of wheezes and crackles can be generated by isolating these sounds from the sound recording, and the trends of these indices can be observed. For example, an index of $T_{wheeze}/T_{total}$ showing the ratio of time that the breathing also includes a wheeze component can be recorded and followed, where a rise in this ratio shows a trend towards a worsening condition. Similarly, "crackles" can be detected and a count of "crackles" maintained, preferably organized according to the breathing phase, such that the number of crackles during the early/late inspiratory phase and during the early/late expiratory phase of the breathing is known, in addition to the total number of crackles. All three of these indices can be monitored for trends, where an increase in the crackle count signifies a deterioration in the condition of the lungs. Early inspiratory and expiratory crackles are the hallmark of chronic bronchitis, whereas late inspiratory crackles may mean pneumonia, CHF, or atelectasis.

These potential problems can then be signaled as alerts to medical personnel 94, caretakers, and/or patients. Such a remote analytics system and method can also factor in additional physiological data (such as ECG and vital signs) and their trends, whether this additional data is collected by the device 5 or other devices.

Experimental Data

Figure 9A:
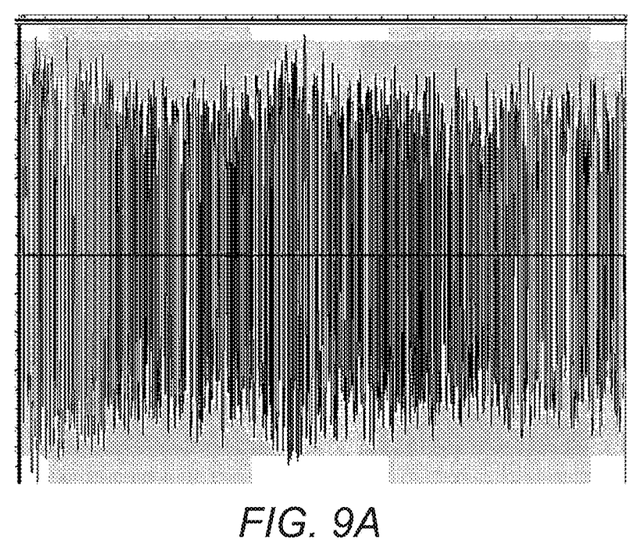
FIGS. 9A-9D show experimental waveforms received from the oral device according to different filtering and noise reduction conditions.

On placement of the device into the mouth and sealing of the lips around it, the microphone was located within the oronasal cavity. The raw sound waveform for several respiratory cycles is shown in FIG. 9A. The high frequency whistling and noise present within the oronasal cavity serve to obscure the underlying sound pattern. However, by applying a high-pass filter set at 1000 Hz to this data, with a roll-off of 6 dB/octave, the received data shown in FIG. 9B clearly shows a typical inspirium and experium pattern as would be heard by applying a stethoscope to the chest.

Figure 9B:
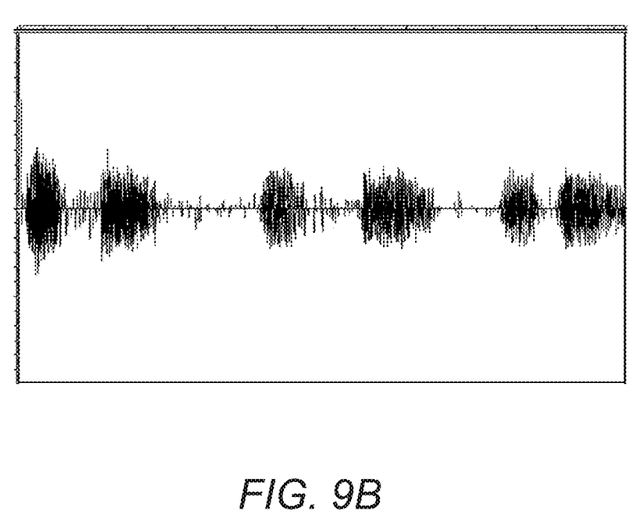
Figure 9C:
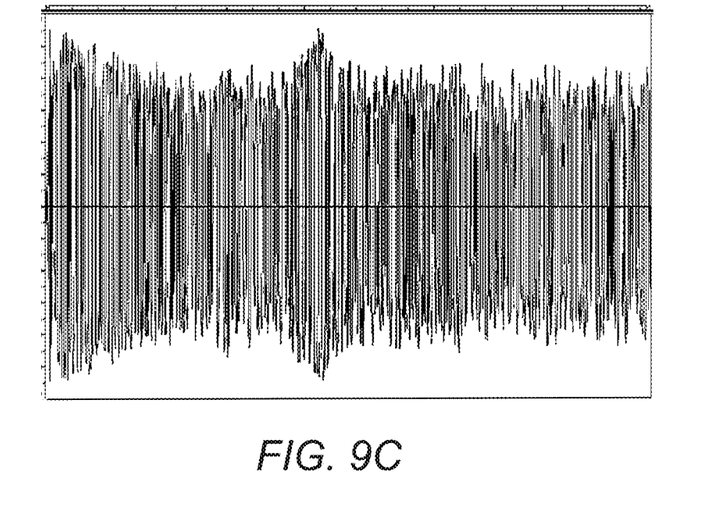

In order to determine the relative importance of the noise reduction, we applied a 16 dB noise reduction with a sensitivity of 6.0, using 3 frequency smoothing bands, with the results being shown in FIG. 9C. We then applied the high-pass filter used above (i.e. 1000 Hz, with a roll-off of 6 dB/octave) to the noise-reduced data, in order to yield the sound wave shown in FIG. 9D.

As is readily appreciated, the signal processing enables the production of an auscultation-type sound wave which is significantly equivalent to that yielded by the use of a stethoscope against the chest in traditional auscultation.

Figure 9D:
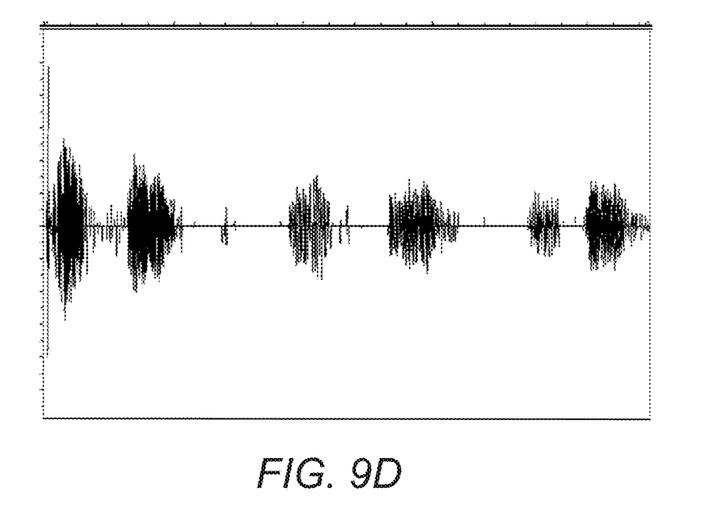

Comparing the experimentally-derived waveforms in FIGS. 9B and 9D to a standard "textbook" illustration of the components of a chest auscultation, as shown in FIG. 7, it is clear that the major components—inspirium, experium, and lung sounds—are all present in the sound wave data, as detected and then processed by an oral device 5 of the current invention.

The oral device 5 enables a physician to perform remote auscultation, by receiving and listening to the sound data file at a remote location. Advantageously, this system enables the performance of remote auscultation to be performed without the traditional requirement for the patient to place an electronic stethoscope on his chest. Essentially, the patient just needs to "take his temperature" and the process of recording, signal-processing and transmission of the data is performed automatically.

The invention claimed is:

1. An oral device for recording respiratory sounds and oral temperature, comprising a handle section and a mouthpiece, said mouthpiece comprising a neck and a tip; said neck is configured for lips of a subject to be wrapped around thereby sealing closed a mouth of said subject during placement of said tip inside the mouth of said subject; said tip further comprises a temperature sensor for sensing oral temperature of said subject;

wherein said mouthpiece further comprises one or more microphones, configured to be disposed inside said mouth and to detect respiratory sounds from an oronasal cavity and/or lungs of said subject during said placement.

2. The oral device of claim 1, further comprising a display.

3. The oral device of claim 2, wherein said oral device is in communicative connection with an information processing system in a location selected from the group consisting of within said oral device, in a cloud server, on a smartphone or any combination thereof, said communicative connection between said oral device and/or said smartphone being wireless, said information processing system configured to calculate a respiratory rate of said patient from a low-frequency periodicity in said respiratory sounds, wherein said display is configured to display said respiratory rate and/or said oral temperature of said subject.

4. The oral device of claim 1, further comprising a member selected from the group consisting of an electrocardiogram (ECG) circuit, a pulse-oximetry sensor, or any combination thereof.

5. The oral device of claim 4, wherein a display is further configured to display pulse rate and/or peripheral oxygen saturation of said subject, measured by said pulse oximetry sensor.

6. A system comprising:
   an oral device for recording respiratory sounds and oral temperature, comprising a handle section and a mouthpiece, said mouthpiece comprising a neck and a tip; said neck is configured for lips of a subject to be wrapped around, thereby sealing closed a mouth of said subject during placement of said tip inside the mouth of said subject; said tip comprises a temperature sensor for sensing said oral temperature of said subject; said mouthpiece comprising one or more microphones configured to be disposed inside said mouth and to detect respiratory sounds from an oronasal cavity and/or lungs of said subject during said placement;
   said oral device being in communicative connection with an information processing system in a location selected from the group consisting of within said oral device, in a cloud server, on a smartphone or any combination thereof, said communicative connection between said oral device and/or said smartphone being wireless; said communicative connection being configured to upload one or more sensed data comprising a lung auscultation; said information processing system being configured to store said one or more of said sensed data comprising said lung auscultation; and said information processing system is in communicative connection with a display device.

7. The system of claim 6, further configured for displaying said lung auscultation on display device remotely disposed from said oral device.

8. The system of claim 7, wherein said information processing system is further configured to analyze and monitor trends of said lung auscultation for evidence of progression of a disease.

9. The system of claim 8, wherein said analysis comprises a ratio of time that breathing also includes a wheeze measurement to total breathing time and/or a count of crackles during breathing.

10. The system of claim 9, wherein said count of crackles is selected from the group consisting of a number of crackles during an early inspiratory phase, a number of crackles during a late inspiratory phase, a number of crackles during an early expiratory phase, a number of crackles during a late expiratory phase, total number of crackles, or any combination thereof.

11. The system of claim 7, wherein said display device is configured to display the lung auscultation, analysis of the lung auscultation, or any combination thereof.

12. The system of claim 6, wherein said wireless communicative connection a 5G modem, a SIM module, a BLUETOOTH®/BLUETOOTH® Low Energy connection, a Wi-Fi® connection, a cellular connection, or any combination thereof.

13. A method for recording respiratory sounds, comprising steps of:
   inserting an oral device into a mouth of a subject, said oral device having a handle section and a mouthpiece, said mouthpiece comprising a neck and a tip; said mouthpiece further comprising one or more microphones;
   wrapping lips of the subject around said neck sealing the mouth of said subject closed during placement of said tip inside the mouth of said subject such that an oral temperature sensor of said tip is under a tongue of the subject, said subject's lips are closed around said neck; and said one or more microphones are inside said mouth during said placement; said microphones detecting respiratory sounds from an oronasal cavity and/or lungs during said placement.

14. The method of claim 13, further comprising one or more steps of: placing said oral device in communicative connection with an information processing system in a location selected from the group consisting of within said oral device, in a cloud server, on a smartphone or any combination thereof, said communicative connection between said oral device and/or said smartphone being wireless; calculating a respiratory rate of said subject from a low-frequency periodicity in said respiratory sounds and displaying said respiratory rate and/or an oral temperature of said subject.

15. The method of claim 14 further comprising a step of providing said oral device with a member of the group consisting of an electrocardiogram circuit, a pulse oximetry sensor, or any combination thereof.

16. The method of claim 15, further comprising a step of displaying a pulse rate and/or peripheral oxygen saturation of said subject measured by said pulse oximetry sensor.

17. The method of claim 13, comprising steps of placing said oral device in communicative connection with an information processing system in a location selected from the group consisting of within said oral device, in a cloud server, on a smartphone or any combination thereof, said communicative connection between said oral device and/or said smartphone being wireless; uploading one or more sensed data comprising a lung auscultation and/or data comprising said respiratory sounds via said wireless communicative connection, storing said one or more sensed data comprising said lung auscultation and/or said data comprising said respiratory sounds; and communicatively connecting said information processing system with a display device.

18. The method of claim 17, further comprising steps of said information processing system analyzing and monitoring trends of said lung auscultation for evidence of progression of a disease.

19. The method of claim 17, further comprising a step of said display device displaying the lung auscultation, analysis of said lung auscultation, or any combination thereof.

20. The method of claim 19, wherein said analysis comprises a ratio of time that breathing also includes a wheeze measurement to total breathing time and/or a count of crackles during breathing.

21. The method of claim 20, wherein said count of crackles is selected from the group consisting of a number of crackles during an early inspiratory phase, a number of crackles during a late inspiratory phase, a number of crackles during an early expiratory phase, a number of crackles during a late expiratory phase, total number of crackles, or any combination thereof.

\* \* \* \* \*